Figure 1:
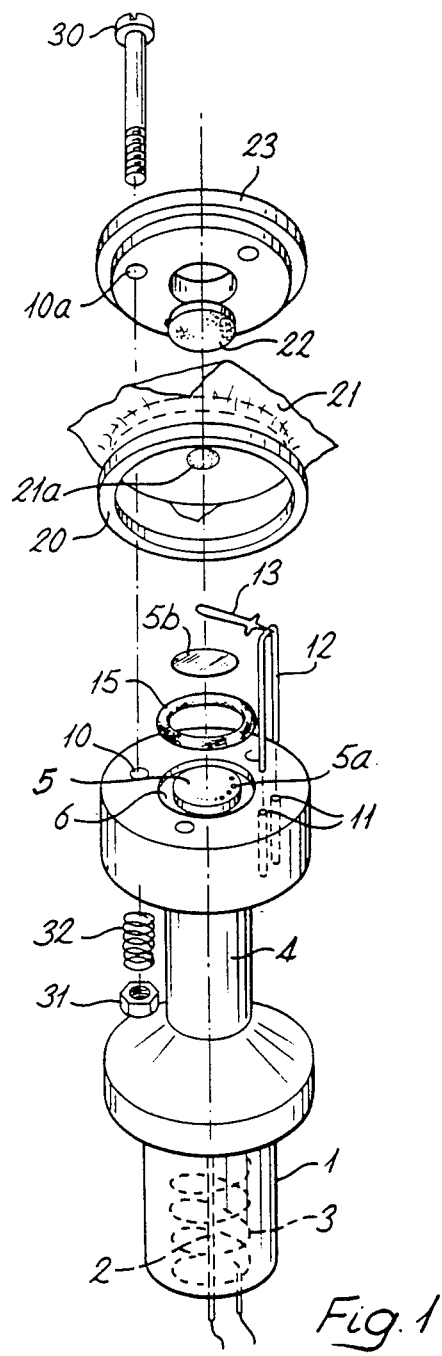

United States Patent [19]

Bergman

[11] Patent Number: 4,632,746
[45] Date of Patent: Dec. 30, 1986

[54] ELECTROCHEMICAL CELL WITH THIN WIRE ELECTRODE

[75] Inventor: Imanuel Bergman, Sheffield, England

[73] Assignee: National Research Development Corp., London, England

[21] Appl. No.: 804,139

[22] Filed: Dec. 3, 1985

[30] Foreign Application Priority Data

Dec. 6, 1984 [GB] United Kingdom ............... 8430803

[51] Int. Cl.⁴ .................... G01N 27/30; G01N 27/50
[52] U.S. Cl. .................................. 204/415; 204/1 T
[58] Field of Search ............. 204/415, 403, 1 K, 1 P; 128/635

[56] References Cited

U.S. PATENT DOCUMENTS 4,498,970 2/1985 Chand ............................ 204/415

Primary Examiner—G. L. Kaplan
Attorney, Agent, or Firm—Cushman, Darby & Cushman

[57] ABSTRACT

An electrochemical cell has an electrolyte container 4 with a wall 5, apertured to let electrolyte soak a membrane 5b. A thin wire loop electrode 13 of (if necessary) precisely known length and cross-section rests on the membrane and contacts a metallised portion 21a of the membrane electrode 21, itself contacting the air through a sinter 22. The loop electrode 13 is sealed into its electrolyte chamber between 21a and 5b by an O-ring 15.

If the electrolyte is acetonitrile, then methane in the air can be detected.

6 Claims, 2 Drawing Figures

U.S. Patent   Dec. 30, 1986   4,632,746

ELECTROCHEMICAL CELL WITH THIN WIRE ELECTRODE

This invention relates to an electrochemical cell having a thin wire electrode.

Such an electrode may be used principally as an amperometric sensing electrode, although it can be used as a potentiometric sensing or reference electrode, or even as a conductimetric electrode. An amperometric sensing electrode is normally held at a defined potential with respect to a reference electrode with which it communicates via an electrolyte, while the current to be measured is carried via the electrolyte and an auxiliary electrode. Many of the uses of a thin wire electrode are likely to involve the reduction of dissolved oxygen, although any reducible or oxidisable material, or any material that can generate a reducible or oxidisable material, can be detected in a gas, in a liquid, or in some cases even on the surface of a solid.

There are three common reasons for making an electrode in an electrochemical cell from thin wire:

(a) The electrode needs to pass into or through a narrow hole or tube or biological cell.

(b) The electrode needs to carry a small current.

(c) The electrode needs to give a signal which is relatively independent of the flow of the fluid from which the species to be sensed is being transported to the electrode.

The current generated at an electrode is normally dependent on the surface area of the electrode. The thinner the wire, the lower the surface area. The sensing current given by an amperometric sensing electrode will normally depend on the rate at which the species to be sensed reaches the electrode.

At an amperometric sensing electrode, the species to be sensed takes part in an electron transfer as it reaches the electrode surface, or soon afterwards, and is thereby changed into another species. A diffusion layer is formed, in which there is a gradient of partial pressure of the species to be sensed. Diffusion to the centre of a large electrode of finite size embedded in a non-conducting solid will take place in a direction normal to its surface; however, diffusion to the edges of the electrode will have a component parallel to the surface of the electrode.

Adhering to the surface of any solid electrode immersed in a liquid is a layer of the liquid, little affected by fluid flow up to very high flow rates. Diffusion to an electrode made so small that its diameter is comparable to the thickness of the adherent layer, will be mostly through the adherent layer, and therefore little affected by fluid flow.

The restriction of the area of an electrode (to achieve this independence from fluid flow) can be achieved by embedding a thin wire electrode such as platinum in a soda glass rod, and polishing the surface. The glass wets the platinum well, and makes a good seal. The thermal coefficient of expansion of the platinum matches that of the glass, whereby the seal is unaffected by changes of temperature. If however the rod is borosilicate glass or a polymer, the seal may be considerably less effective; likewise where platinum is replaced by a metal more suited to the application than platinum, for example, gold for amperometric oxygen sensors.

Even when the seal between an embedded thin wire electrode and its embedding medium is good at first, it does not usually remain so. Polymers have much larger coefficients of thermal expansion than have metals. Polymers also suffer from creep. The region around the seal suffers from stress-corrosion cracking. The electrolyte may swell or dissolve the embedding medium. Any imperfection in the seal of an embedded fine-wire electrode will mean a change in the surface area of the electrode that is large when compared with its small initial surface area. The media for embedding electrodes may contain materials that will leach out into the electrolyte, even after the media have been polymerised, and these materials may be adsorbed onto the electrode, lessening its catalytic activity.

One use of a very small amperometric electrode is the monitoring of the evolution or uptake of oxygen in a closed chamber by a biological material or system. For instance it may be desired to monitor the evolution of oxygen from a small portion or structure from a leaf when illuminated, or the oxygen uptake of a cell or tissue culture. (Increasingly, cell or tissue-culture techniques are being developed to replace expensive and unpopular animal testing of the likely effect of drugs on humans). Because the oxygen uptake may be small, it may be necessary to conduct the experiment in a closed chamber. It will be undesirable for a significant rate of decrease of the oxygen concentration to be the result of the operation of the amperometric electrode itself. Such an undesirable interference will be minimised by the use of a very small electrode.

When oxygen or other such materials are to be monitored while they are dissolved in a solution, the electrode may be covered with a thin membrane of a non-porous but gas-permeable material such as silicone rubber or PTFE, to prevent interference from materials in the biological solutions. When the oxygen or other such materials are to be monitored in the gas phase, and these remarks apply also the cell according to the invention, the electrode may be clamped between a dialysis membrane (by which phrase we include also other solid electrolyte, or a porous membrane or material filled with electrolyte) and a thin gas-permeable membrane (porous or non-porous), preferably supported on the gas side by a bronze or other sinter. A porous membrane is normally more permeable and gives higher currents. However, unlike a non-porous-membrane electrode, it forms an undesirable complicated three-phase boundary of electrolyte, membrane and gas, and it allows access through the pores of a range of unwanted gaseous or particulate materials, as well as the species of interest.

According to the present invention, there is provided an electrochemical cell comprising: a container, a wall member at least in part permeable to a desired species, the wall member closing the container, an electrolyte, and an electrode immersed in the electrolyte, characterised in that the electrode is of, or is fed by, wire thinner than 0.2 mm diameter and that the length of the wire in contact with the electrolyte is limited by a resilient sealing ring compressed between the container and the wall member, wherein the ring, the container and wall member define a volume containing the electrolyte and into which the wire protrudes.

Preferably the wire is in the form of a loop, both ends of the wire being outside the defined volume. Where the wire is not itself the electrode, the electrode is preferably a metal-coated membrane bounding the said volume.

Preferably the end(s) of the wire is (are) welded to a relatively thick contact wire outside the closed volume.

The sealing ring may be an O-ring or an element formed integrally with the container or wall member.

Alternatively, the wire has a coating of an electroactive material. The concept of 'modified electrodes', i.e. coated (e.g. by deposition) in this way, is known, and the present electrode lends itself very well to such deposition.

The electrode assembly may for example consist of a loop of thin wire, 25 micrometers in diameter, about 20 mm long, welded to the centre of a 'staple' of a contact wire, normally 0.5 mm in diameter, and about 60 mm long. This assembly, weighing about 100 mg, can easily be weighed to the nearest microgram. The deposition can then be carried out on a portion or almost all of the thin wire loop, and the assembly weighed again. If the deposition is carried out by dipping the thin wire into a fluid, the deposition can be carried out such that all the wire that is within the said closed volume has been treated, or only a portion of it, depending on how deep the loop has been dipped.

Enzymes can be highly specific for particular materials; enzyme-containing layers can be deposited on amperometric electrodes, to make the latter specific also, for example to monitor glucose (such as in an artifical pancreas for diabetics). A layer of enzyme-containing material is deposited on the electrode surface or on a thin fabric covering the electrode. In a fluid containing a known amount of oxygen, the presence of glucose will result in a defined reduction of oxygen partial pressure, which can be monitored with the electrode. If the enzyme is deposited on the fabric, the electrode can provide a stable and easily fabricated oxygen electrode. If the enzyme is deposited on the electrode, the electrode provides a format that makes such deposition easily controlled and automated.

The electrode may be a metallised membrane electrode (MME). A known MME consists of a porous film of electronic conductor, usually a metal, deposited by evaporation or sputtering on to a nonporous but gas-permeable membrane of a material such as PTFE. Ideally, the whole of the area of the MME is tightly clamped between an electrolyte-soaked dialysis membrane or other solid electrolyte on the metallised side, and a porous metal sinter on the gas side. The electrolyte needs to be contained, that is to say prevented from leaking out of the cell. With the present cell, the O-ring seal provides such a containment, and the thin wire provides a reliable contact to the metallised film. When a metal sinter is used for clamping the MME, the present electrode enables all of the metallised film to be exposed to the gas being monitored. By means of a mask, the area to be metallised is restricted to the centre of the area to which there is access of electrolyte via the dialysis membrane, and access of the gas to be monitored via the sinter and PTFE membrane. This gives an optimum ratio of response signal to background signal in the absence of the gas being monitored.

An example of a fast-responding MME uses a PTFE membrane 3 micrometers thick directly exposed to the gas being monitored, i.e. without any intervening sinter. The edge of the central 2.5 mm hole exposed to the gas is covered with a thin rubber gasket. The metallised area is in the form of a central disk 5 mm in diameter, with two radially protruding 3 mm-long 1 mm-wide arms; i.e. a propeller shape. The electrode wire loop is shaped around but not into the pipe forming the opening to the gas phase, to pass over the thin rubber gasket, and make contact to the arms of the metallised area. In this way, the edge of the gas pipe cannot accidentally cut the thin wire electrode as the cell is assembled.

The sealing ring may be integrally formed with the container body as an annular protrusion. This may be especially suitable if the container body itself is made for high-temperature use, such as of PTFE or other injection moulded or machinable material; this can lessen problems with differential thermal expansion.

The sealing ring, preferably however being an O-ring, may be of 1.6 mm cross-section and 10.1 mm internal diameter. Preferably it is so mounted that (i) it goes around a cylindrical part protruding into the electrolyte volume and preventing the ring from contracting radially inwardly; and (ii) it is supported 'underneath' by a flange on the cylindrical part; and (iii) it is compressed from 'above' by the said wall member, the electrode passing into the electrolyte volume between the ring and the wall member.

The output of the cell is linear with partial pressure of oxygen up to the normal 21% of an atmosphere in air, to a degree that is better than the instruments normally used to generate a variety of mixtures of gases. However, when a calibration is extended to a partial pressure of one atmosphere of oxygen, the output of the cell deviates significantly from linearity. Unlike most non-linear gas monitors the output is not lower than expected, but higher than expected. This non-linearity is almost certainly caused by heating of the diffusion-limiting membrane by the relatively high current given by a thin membrane and a high concentration of oxygen. A cell incorporating an equally thin membrane, but also a bronze sinter, shows only a small non-linearity. This is presumably because the sinter acts as a heat sink. It should be possible to lessen the non-linearity, without significantly decreasing the speed of response, by blackening the surface of the membrane exposed to air with soot, or otherwise increasing its emissivity for infra-red radiation.

Contact to the thin wire will, as indicated, normally be made outside the O-ring, and the electrolyte will be found inside the O-ring. However, if appropriate the electrolyte could be outside the O-ring, and the contact inside.

In principle, the present cell could be used to monitor an active species dissolved in a liquid stream directly, without any intervening membrane, as long as the liquid was an ionic conductor, and could be fitted with other electrodes. For instance, the oxygen content of a stream of boiler-feed water could be monitored by passing the water through two flanged tubes, with the electrode clamped between the flanges with an O-ring. However, it would normally be desirable to restrain the thin wire from undue movement by clamping it between two fabric mesh screens, over which or through which the liquid stream was flowing.

An amperometric oxygen sensor will register the fall in oxygen partial pressure owing to dilution of the oxygen, when an oxygen-containing gas is humidified. However, there may be an extra effect over and above that of dilution of the oxygen by the water vapour. Under some conditions a film of water appears to form on the surface of the diffusion-limiting membrane. This film appears to act as a diffusion barrier by increasing the energy necessary for transfer of oxygen from the gas phase. The oxygen molecules need to be transferred from the gas phase to a sort of aqueous phase, and then to solution in the PTFE. With membranes of PTFE of thickness between 3 and 12 micrometers, it was found that compression of the PTFE appeared to aggravate, and stretching of the membrane to ameliorate, the interfering effect of water vapour. This is believed to be because even nominally pinhole-free membranes of PTFE between 3 and 6 microns thick have some porosity. When the PTFE is stretched, water molecules from the aqueous electrolyte will pass through and prehumidify the gas being sensed, to a more constant level regardless of its initial humidity.

The thin wire electrode or electrode contact does not need to be a circular-section wire; it can be a thin strip. If the thin strip is of a metal such as gold made by rolling wire into shape, the catalytic activity of the surface of the metal might be affected by the rolling process. The surface area of the strip per unit length would be greater than the original wire. On the other hand, a strip whose back was pressed flat against an impermeable surface would not be available for interaction with a gas diffusing towards the front of the strip.

Figure 2:
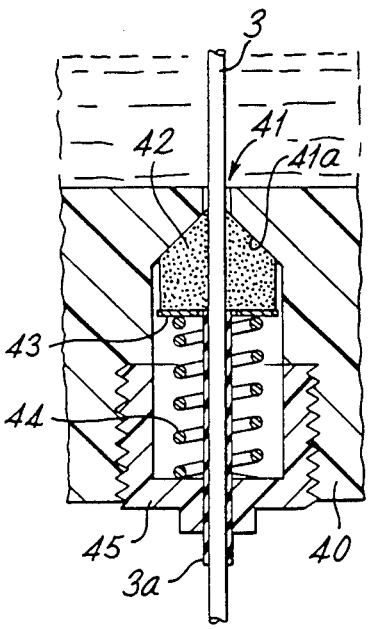

This invention will now be described by way of example with reference to the accompanying drawing, of which:

FIG. 1 shows a schematic exploded view of a cell according to the invention, and FIG. 2 is a detail of a part of the cell of FIG. 1.

Turning to FIG. 1, an electrolyte reservoir 1 contains also a reference electrode 2 and an auxiliary electrode 3 (which may be of wire or foil, for example) and is sealed to a container body 4 by an O-ring (not shown). (The auxiliary electrode 3 enters the reservoir 1 through a seal described with reference to FIG. 2. Alternatively, the reference electrode 2 or both could do so.)

On a central plinth 5 of the opposite face of the container body 4, holes 5a (some omitted for clarity) are drilled near the periphery of its face (leaving the centre undrilled) to communicate with the electrolyte reservoir 1. The plinth 5 is surrounded by a groove 6, itself surrounded by a circle of holes 10 for receiving clamping bolts, further holes as necessary for receiving such ancillary features as thermistor leads and in particular two holes 11 for receiving a working electrode feeder staple 12. The groove 6 receives an O-ring 15, which is thicker than the groove is deep.

A dialysis membrane 5b covers the drilled plinth 5 and against this membrane a wire loop 13 or a metallised-membrane electrode is clamped; the membrane constitutes a sort of electrolyte salt bridge or even a semi-solid or solid electrolyte. It may be made of any suitable ionic conductor, such as regenerated cellulose, swollen with an electrolyte solution, or a porous material such as membrane filter e.g. of PTFE, of suitable pore size, and/or may be hydrophobic, or an ion-exchange membrane such as Nafion (trade mark of du Pont). Nafion is boiled in order to swell it with water, and cellulose is soaked in water in order to remove the glycerol that is used to keep it flexible while it is stored dry.

The feeder staple 12 is of 0.5 mm wire and, when pulled tight through the holes 11, its legs are twisted to hold it fast. A short loop 13 of 25-micron wire is welded to the centre of the crosspiece of the staple 12 and part of the loop is within the circle defined by the O-ring 15. The loop 13 could alternatively be of wire rolled flat (thus for example 10 microns×40 microns).

A clamping ring 20 holds a polytetrafluoroethylene membrane 21 and a sinter 22 in place against an end plate 23 provided with bolt holes 10a which align with the holes 10 on the container body 4. Bolts 30 (only one shown) pass through the holes 10a and 10 and are secured by nuts 31 which compress springs 32 to apply a resilient clamping force compressing the O-ring 15 which thereby seals a volume defined by the plinth 5, the O-ring 15 and the membrane 21 despite the intrusion of the loop 13 into that volume. The volume contains a disc 5b of dialysis membrane sitting on the plinth; the springs 32 thus also clamp the membrane against the 'solid electrolyte', giving a stable and effective amperometric electrode. The groove 6 prevents the O-ring 15 from contracting radially inwardly, which would tend undesirably to pucker the membrane 21.

The springs for clamping the gas-permeable membrane to the O-ring are important. The clamping pressure needs to be sufficiently great to prevent leakage of electrolyte out past the O-ring and of electrochemically active species into the electrolyte near the electrode. There appears to be a minimum clamping pressure that need to be applied to the gas-permeable membrane to clamp the metal of the electrode against the dialysis membrane, in order to achieve an ideal polarogram in the polarographic or amperometric cell in which it is incorporated. The balance between the clamping pressures to be applied to the O-ring and to the area of the cell inside the O-ring, is achieved by adjusting the depth of the O-ring recess and the thickness of the dialysis membrane and of the disc of filter paper that is routinely placed under the dialysis membrane in the latest design of cell. The use of a spring or springs is also important because the polymers used as chemically inert and electrically insulating containers tend to creep under pressure, and to have coefficients of thermal expansion high even compared to metals.

The electrode formed by the loop 13 fed by the staple 12 can thus detect gas which has diffused through the sinter 22 and the membrane 21 to interact with the surface of the electrode, which itself has been wetted with the electrolyte which has passed through the holes in the plinth 5 to bathe the loop 13.

Certain points of detail regarding this structure are as follows:

The PTFE membrane 21 is stretched by mounting it on the end plate 23 which constitutes the front face of the electrochemical cell. The clamping ring 20 is of polychlorotrifluoroethylene Kel-F and is an interference fit over the end plate; when forced over the plate, it holds the stretched membrane in place. This method of mounting the membrane has proved to be particularly convenient also for inspecting the membrane for flaws, and for subsequent evaporation or sputtering of metal layers onto membranes for use in metallised-membrane electrodes. If the membrane 21 is metallised in this way (on its lower surface as drawn), it forms a film electrode 21a, but the wire loop 13 is still present, and feeds the film electrode 21a formed on the membrane 21. The film electrode 21a is significantly smaller than the sinter 22 and than the disc 5b and thereby determines the sensitivity to gas and minimises the background current.

The electrode loop 13 normally consists of a fine wire, although a carbon fibre or other electronic conductor could be used. The wire diameter is typically 25 micrometers. Gold wire of this diameter is readily available because of its use in the manufacture of semiconductors, but other materials are possible, e.g. platinum, palladium and silver. An alloy of 30 weight % silver in gold is usable, being stronger than pure gold but more resistant to oxidation than silver. The thin wire electrode is normally used in the form of the loop 13, although this is not essential. The length of wire in contact with the electrolyte has typically been 20 mm, although this dimension is not critical. A convenient way of massproducing thin wire loops is to weld them on to a 'header' wire in the form of a long 'staple' 12. The staple 12 has been made from 0.5 mm diameter wire of silver or of the nickel alloy commonly used for the legs of circular-can transistors. The staple is typically in the form of a crosspiece 5 mm long, and two legs, each 30 mm long. The thin wire is welded to the crosspiece, and the legs are pushed through the two holes 11, typically 1 mm diameter, in the body of the electrochemical cell. The legs are then twisted together to keep the staple in place, and soldered to the wire connecting the electrode to a circuit. When the cross-piece of the staple is to fit into a circular groove in the face of a cell, the staple can be shaped by clamping it between the two faces of a jig which has such a circular groove, as well as the two 1 mm holes through which the staple normally fits.

A useful form of the thin wire loop 13 is with slack of 1 or 2 mm in both limbs of the loop between the staple and the O-ring, so that the wire is not stretched when it is clamped against the O-ring. The end of the loop may be a semicircle of 6 mm diameter. The loop may be shaped by rucking it with tweezers.

The O-ring 15 may be a vinylidene fluoride/hexafluoropropylene copolymer, popularly known as VITON rubber, because this material has a good resistance to a variety of chemicals, and does not contain catalyst poisons such as sulphur.

O-rings are normally clamped between two surfaces only. In the cell according to the invention, however, a circular O-ring groove 6, in which the O-ring 15 is prevented from reducing its diameter, is cut into that face of the container body 4. The thin wire 13 is clamped between this O-ring and the flat face of the gas-feed end plate 23, normally made of polymethylmethacrylate or of polychlorotrifluoroethylene covered with the non-porous but gas-permeable membrane 21. The O-ring 15 is thus restrained on three or even four points around the circumference of its minor cross-section. The fact that the O-ring cannot reduce its major diameter when it is clamped is important, in that it prevents the O-ring exerting any inward force on the gas-permeable membrane against which it is clamped. Any such force would oppose the stretching of the membrane, desirable for minimising the adverse effects of moisture on the diffusion of oxygen through the membrane.

There are two favoured designs for the supports for the dialysis membrane 5b:

(a) A ring of holes 5a near the periphery of the flat face of the plinth 5 communicates with the electrolyte reservoir containing the reference and auxiliary electrodes. A disc of fine filter paper or porous PTFE membrane filter is cut to fit loosely inside the O-ring 15 and is laid on this central region. A dialysis membrane swollen with water is also cut to fit loosely inside the O-ring. Its central region is pierced with a fine needle in several places and it is laid on the filter paper. If the dialysis membrane is made of a porous material, piercing is unnecessary. The feeder staple 12 is then fitted into its two holes 11, and the loop 13 is positioned to lie flat on the dialysis membrane. If the end plate 23 has a central hole with a rubber membrane gasket, communicating with the atmosphere without a bronze sinter, then the thin wire loop 13 must be positioned accurately around the central region, so that when the cell assembly is clamped together, the wire loop will make contact to the central metallised region, without overlapping the hole.

(b) The plinth 5 is a detachable polymethylmethacrylate cylinder whose circumferential surface carries axial grooves, providing electrolyte channels between its plane surfaces. This plinth sits on the base of the recess leaving, round it, a groove 6. This base has a channel machined around its periphery, in which are drilled a ring of holes communicating with the electrolyte reservoir 1 containing the reference and auxiliary electrodes 2 and 3. A polymethylmethacrylate ring, in which the plinth fits loosely, is used to shape a captive dialysis membrane. A 30 mm diameter disc of wet cellulose dialysis membrane material is laid over the ring, which contains a smooth faced cylinder. The plinth is pressed against the face of this cylinder with a 10 mm diameter disc of filter paper in between, such that the plinth enters the ring to a depth of 3 to 4 mm, with a cap of dialysis membrane trapped between them. The frills of excess dialysis membrane are trimmed off with a scalpel, and the plinth, with its cap of dialysis membrane, is pushed into the centre of the annular ring. The dialysis membrane is then pierced with a fine scalpel blade over the end of each groove in the plinth, and a number of times with a fine needle over the area to be covered with an amperometric electrode, to relieve osmotic pressure which would otherwise tend to distort it. The dialysis membrane is then allowed to dry naturally, or is dried quickly in a vacuum in a bell jar. The plinth, with its captive smooth dialysis membrane face upwards, can then be installed in the recess in the cell face. One advantage of the detachable plinth design is that the cell can be assembled dry, and the electrolyte added later.

The dialysis membrane has been described in terms of materials such as regenerated cellulose and Nafion swollen with an aqueous electrolyte to give a smooth elastic ionic conductor, which can act as a salt bridge or solid electrolyte. In fact a porous material such as a membrane filter or a filter paper could be used to support the electrode or even a metallised-membrane electrode on the electrolyte side. The more a material is permeable via pores rather than via a process of dissolution of the permeating species in the material, the less discrimination there is between the permeation of desirable and undesirable species.

With high current-systems, or those in which rapid changes of voltage are necessary, cell resistance between an amperometric metallised-membrane electrode 21 and the reference electrode 2 should be well below, say, 500 ohms. One approach is to incorporate a metal-sheet or metal-film electrode with a separate thin wire contact, below the dialysis membrane. The dialysis membrane can be made very thin, and the resistance between metallised-membrane electrode 21 and the sheet electrode can be made very low (say 10 ohms), although in some cases it would not be possible to have a low resistance, for example if acetonitrile were used without a supporting electrolyte, when the resistance could be megohms.

Typical materials from which the body 4 and the other parts of the cell are made are polymers having very high thermal coefficients of expansion and creeping under pressure. The cells operate best when they are tightly clamped, but the clamping pressures will change with temperature and will anyway be lowered by creep. The use of the springs 32 overcomes this.

Multiple thin wire electrodes can be fitted in a single cell assembly. The only limitation on the number of electrodes is that of finding room for the contacts and the electrodes without any short circuits. The electrodes could be either single wires or loops. The electrodes on the gas side of the dialysis membrane would normally be either sensing electrodes or guard electrodes. The guard electrodes would normally be designed to prevent interfering materials reaching particular electrodes along the face of the dialysis membrane. The sensing electrodes could be either amperometric, potentiometric or conductimetric. Reference electrodes would normally be best placed on the electrolyte reservoir side of the dialysis membrane, or in the electrolyte reservoir itself, although they would operate satisfactorily if they were mounted on the same side of the dialysis membrane as the sensing electrode. Auxiliary electrodes would normally be placed into the electrolyte reservoir. In some circumstances it would be undesirable to place the reference electrode too near the auxiliary electrode, in case materials generated at the latter would interfere with the reference potential of the former. Of course they could be separated by an additional dialysis membrane, which could be porous. Multiple thin wire electrodes can be mounted not only on either side of the dialysis membrane, but between multiple layers of dialysis membrane, of a variety of thicknesses, if it was desirable to prevent or at least minimise, the diffusion of materials from one electrode to another.

One application of multiple thin wire sensing electrodes is in the simultaneous sensing of a number of gases with the same cell. Each amperometric thin wire electrode, with its own potentiostat and current-to-voltage converter, would be set to a different potential with respect to a reference electrode. Alternatively, separate isolated portions of the area of a membrane electrode may be metallised, with separate circuitry to each metallised portion. Such membrane electrodes could even be stacked one behind the other.

Placing both reference and auxiliary electrodes against the dialysis membrane could have the following advantages:

(a) Cells may lose electrolyte by evaporation or by leakage. Bubbles between electrodes may cause electrical noise by their movement, or just undesirably high resistance. If, however, the reference and auxiliary electrodes were also placed against the dialysis membrane, especially if a wick or other electrolyte-absorbent material covered the reference and auxiliary electrodes, the cell would be protected from interference by bubbles and protected from loss of electrolyte solution until the dialysis membrane itself started to dry out.

(b) The ion-exchange membrane Nafion is itself a solid electrolyte when swollen with water. There is a commercially available amperometric sensor in which a number of electrodes have been deposited on to the surfaces of a Nafion membrane, which itself has access to water in a reservoir. Similarly, thin wire electrodes could be clamped against a Nafion membrane with access to a water reservoir. The majority of metallised-membrane and thin wire electrodes tested so far have involved electrolytes of saline or dilute sulphuric acid. A cell with all electrodes mounted on the Nafion membrane needs no such electrolyte solutions; water is sufficient.

In the example, the cell has been described in terms of a groove 6 cut into the face of the container body 4 of the cell, and an O-ring 15 protruding from this groove. In principle, the O-ring groove could be in the front plate of the cell, and the O-ring could be set into this latter groove. This arrangement is not normally as convenient as having the groove in the front face of the cell. However, as already indicated, a further possibility, if the cell body or front plate were made of a suitable material, is to substitute a ridge protruding from the surface of the component for an O-ring protruding from a groove in the surface. This ridge might be of semi-circular cross-section, like a protruding O-ring, or of triangular or other cross-section. Such a ridge could be machined on the face of the cell body or on the front plate, or could be incorporated into a component that was fabricated by a process such as injection moulding.

Turning to FIG. 2, the auxiliary electrode 3 enters the container body 1 through the container wall 40, which is often made from a polymer. Polymers normally have coefficients of expansion much greater than those of metals. Some also suffer from creep when exposed to clamping forces. These properties make sealing electrodes into polymer cells difficult.

Electrode contacts in the form of robust sheets, or of rods of diameter greater than about 2 mm may be sealed into polymers by means of elastomeric O-rings. However, most elastomers of reasonable price withstand neither temperatures above 200° C. nor the non-aqueous solvents that are most useful in electrochemistry.

However, it is here desirable to seal the electrode 3 made of gold or platinum through the polymeric cell wall 40. Because of expense or weight, it will be desirable to use a wire of about 0.5 mm diameter. The present invention uses the polymer PTFE, which can operate in high temperatures and in corrosive solvents, to seal such an electrode wire into a cell.

At the top a hole 41 in the wall 40 is drilled to give clearance to the wire 3. The hole then widens gradually downwards to give a conical seat 41a for the seal. This portion contains a conical component 42 made from PTFE with a push-fit hole for the wire. A metal washer 43 is placed against the conical component 42. The centre of the washer has a hole which gives clearance to the wire, and to an insulating sleeve 3a around the wire.

As the hole proceeds downwards, there is then a cylindrical portion in which a cylindrical coil spring 44 is placed. The wire, with its insulating sleeve, fits into the inside of the coil spring. The hole then widens further into a threaded portion, into which a special screw 45 is fitted. This screw, at its upper end, has a portion into which the lower end of the spring fits. The lower end of the screw has a hole through which the wire, with its insulating sleeve, can pass.

The screw will need to be fitted into the cell body or lid after the electrode wire 3 has been fitted. There are two possibilities for tightening the screw to clamp the spring to allow the conical PTFE component to seal itself around the wire and against the conical seat in the cell wall. One (as shown) is to allow the screw to protrude below the bottom face of the cell, and shape two flats on the screw, which will allow the screw to be turned with a spanner. An alternative (not shown) is to make a special screwdriver, with a central hole to allow the wire to pass, and with two pins fitting into holes on opposite sides of the bottom face of the screw.

This electrode seal can be used for relatively thin wires; the spring 44 maintains the seal even when polymeric components creep, or vary considerably in thermal expansion from the metallic components or from each other.

One use for the cell just described is as follows.

Continuous-reading methane sensors are normally based on infra-red absorption, or catalytic combustion. The combustion is normally sensed by an increase in heat output on or near a resistance thermometer, or a change in the conductivity of a semiconductor. Both infra-red and combustion sensors need too much power to be intrinsically safe.

In principle, an amperometric sensor for methane could easily be made intrinsically safe, as long as it did not need to operate at too elevated a temperature. One potential advantage of the amperometric system would be that the eight electrons donated by the complete oxidation of one methane molecule could be transformed directly into a detection current. The potential applied to the sensing electrode would correspond directly to a change in energy towards the ionisation of the methane.

The possibility existed that a non-aqueous solvent such as acetonitrile might enable methane to be oxidised at ambient temperatures on a platinum metallised-membrane electrode (MME), but acetonitrile was said to attack most polymer resins and elastomers, such as those used in the standard designs of the MME. However, PTFE resists acetonitrile, and in certain grades could be more easily machined than the standard material commonly available. In this cell, the electrolyte comes into contact only with the PTFE body and with PTFE membranes.

The auxiliary electrode was a platinum wire, flattened with jewellers' rollers so that it could be sealed into the cell with an O-ring protected by a 50 micron thick PTFE film. The reference electrode was a platinum film sputtered on to a PTFE membrane filter, placed below another non-metallised membrane filter, which acted as a salt bridge instead of the dialysis membrane. The reference and sensing electrodes were each contacted with a 25 micron thick platinum wire loop.

The cell shows no signs of attack by the acetonitrile electrolyte. Polarograms of nitrogen and of methane show a clear response to methane in the anodic region. Methane and ethylene both give responses of about 10 nA. Ethylene gives much larger responses in aqueous electrolytes. This may indicate that the oxidation involves only small numbers of electrons per molecule in acetonitrile.

Many enquiries have been received over the years for amperometric sensors whose electrolyte would not freeze easily. The freezing point of acetonitrile is below 40° C.

No ionic material dissolved in the solvent is used as supporting electrolyte. This is to avoid an undesirable contribution to the background current form the oxidation of such ionic material. A high-impedance high-voltage-output potentiostat is used with the high-resistance acetonitrile electrolyte.

What is claimed is:

1. An electrochemical cell comprising: a container,
   a wall member at least in part permeable to a desired species, the wall member closing the container,
   an electrolyte, and an electrode immersed in the electrolyte,
   characterised in that
      the electrode is of, or is fed by, wire thinner than 0.2 mm diameter,
      the length of the wire in contact with the electrolyte is limited by a resilient sealing ring compressed between the container and the wall member, wherein the ring, the container and wall member define a volume containing the electrolyte and into which the wire protrudes, and
      said wire is in the form of a loop having two ends, both of which are disposed outside said volume.

2. An electrochemical cell according to claim 1, wherein the electrode is a metal-coated membrane bounding the said volume.

3. An electrochemical cell according to claim 1 wherein the sealing ring is an O-ring.

4. An electrochemical cell according to claim 1, wherein an electrode current feeder member enters the container through a frusto conical aperture sealed by a conical bung under compression.

5. An electrochemical cell according to claim 1, wherein the electrolyte is acetonitrile.

6. An electrochemical cell according to claim 1, wherein:
   outside said volume, at least one end of said wire is connected to a respective contact wire which is substantially thicker than said wire.

* * * * *